United States Patent
Fukagai et al.

(10) Patent No.: US 7,614,392 B2
(45) Date of Patent: Nov. 10, 2009

(54) DIAGNOSTIC METHOD AND CONTROL APPARATUS FOR GAS SENSOR

(75) Inventors: Reina Fukagai, Aichi (JP); Norikazu Ieda, Ichinomiya (JP); Masahiro Tanaka, Kasugai (JP); Hiroshi Inagaki, Komaki (JP); Kunihiko Takamatsu, Toyota (JP); Masaki Hirata, Hamamatsu (JP); Takahiro Suzuki, Hamamatsu (JP)

(73) Assignees: NGK Spark Plug Co., Ltd., Nagoya-shi, Aichi (JP); Suzuki Motor Corporation, Hamamatsu-shi, Shizuoka (JP)

( * ) Notice: Subject to any disclaimer, the term of this patent is extended or adjusted under 35 U.S.C. 154(b) by 86 days.

(21) Appl. No.: 12/033,525

(22) Filed: Feb. 19, 2008

(65) Prior Publication Data
US 2008/0196702 A1    Aug. 21, 2008

(30) Foreign Application Priority Data
Feb. 21, 2007   (JP)   ............................. 2007-040919
Aug. 23, 2007   (JP)   ............................. 2007-217392

(51) Int. Cl.
*F02D 41/22*    (2006.01)
(52) U.S. Cl. .................... 123/688; 123/481; 60/276; 701/109
(58) Field of Classification Search ................ 123/436, 123/672, 690, 693, 703, 481, 688; 701/107, 701/109, 103; 60/276
See application file for complete search history.

(56) References Cited

U.S. PATENT DOCUMENTS

| 5,179,924 A | 1/1993 | Manaka |
| 5,672,817 A | 9/1997 | Sagisaka et al. |
| 7,266,942 B2 * | 9/2007 | Iihoshi et al. ................. 60/277 |

FOREIGN PATENT DOCUMENTS

| JP | 4-36651 A | 2/1992 |
| JP | 8-177575 A | 7/1996 |
| JP | 2003-185626 A | 7/2003 |
| JP | 2008-169776 | * 7/2008 |

* cited by examiner

*Primary Examiner*—Hai H Huynh
(74) *Attorney, Agent, or Firm*—Flynn, Thiel, Boutell & Tanis, P.C.

(57) ABSTRACT

A gas sensor diagnostic method includes: a fuel supply detecting step of detecting an interruption of a fuel supply to the internal combustion engine, and a restart of the fuel supply after the interruption of the fuel supply; a response time period accumulating step of determining a response time period by accumulating a first time period that the sensor output value reaches from a first threshold value to a second threshold value after the detection of the interruption of the fuel supply, and a second time period that the sensor output value reaches from a third threshold value to a fourth threshold value after the detection of the restart of the fuel supply after the interruption of the fuel supply; and an abnormal state diagnosing section of determining an abnormal state of the gas sensor when the response time period is greater than a predetermined time period.

8 Claims, 8 Drawing Sheets

DIAGNOSTIC METHOD AND CONTROL APPARATUS FOR GAS SENSOR

BACKGROUND OF THE INVENTION

This invention relates to an abnormal state diagnosis method for examining whether or not a gas sensor disposed in an exhaust passage of an internal combustion engine is in an abnormal state, and/or gas sensor control or diagnostic apparatus for such a gas sensor.

A three-way catalyst is widely used in internal combustion engines for motor vehicles and other applications, to purify CO, HC and NOx contained in exhaust gas mixture. Furthermore, in order to improve the efficiency of the purification, there is provided a feedback air-fuel ratio control system including a gas sensor disposed in the exhaust passage of the engine, for sensing the oxygen concentration in the exhaust gases, and a controller for controlling the mixture ratio or air-fuel ratio toward the theoretical air-fuel ratio by regulating a fuel supply quantity, such as a fuel injection quantity, to the engine in accordance with the sensed oxygen concentration. Recently, the feedback air-fuel ratio control system often employs, as the gas sensor, a wide-range or full-range air-fuel ratio sensor varying the sensor output linearly in accordance with the oxygen concentration in the exhaust gases, in order to improve the accuracy of the feedback control.

In a case in which the gas sensor is used for a long time period, there may be generated the time degradation such as a clogging of gas through holes formed in a protector of the gas sensor (protector for covering and protecting periphery of the sensing element), and porous portions for introducing the exhaust gas into the sensing element. By this degradation of the gas sensor, a response of a sensor output outputted in accordance with a concentration variation of a specified gas component in the exhaust gas becomes slow relative to a gas sensor (in a normal state) which is not deteriorated. Accordingly, this degradation may cause problems that the fuel economy is deteriorated, and that the exhaust gas is not sufficiently purified. Therefore, there are proposed methods of the deterioration diagnosis of the gas sensor by using sensor output value of the gas sensor.

For example, published Japanese Patent Applications, Publication Numbers H4-36651 and H8-177575 propose an air-fuel ratio control method and a self-diagnostic apparatus of an air-fuel ratio control system configured to diagnose whether or not the gas sensor is in the abnormal state by using a variation of the output of the gas sensor which corresponds to a start of an interruption of a fuel supply to an internal combustion engine, and a restart of the fuel supply after the fuel supply interruption.

SUMMARY OF THE INVENTION

However, in recent year, it is desired to improve the accuracy of the degradation diagnosis of the gas sensor, and for example, to sense a degradation state (abnormal state) of the gas sensor before the gas sensor is severely deteriorated. However, the variations of the sensor output value after the fuel supply interruption and after the fuel supply restart differ only slightly in the normal state and in the slight degradation state. Therefore, it is difficult to set a threshold value for judging the normal state or the slight degradation state by using either the variation of gas sensor output after the fuel supply interruption or the variation of the gas sensor output after the fuel supply restart as in the conventional manner. It may be not possible to accurately diagnose the abnormal state of the gas sensor. Specifically, in a case in which a feedback control of the internal combustion engine is performed at a target air-fuel ratio set to a lean region relative to the theoretical air-fuel ratio, the variations of the sensor output values after the fuel supply interruption and after the fuel supply restart are gentle. Accordingly, there is a little difference between the sensor output values in the normal state and the degradation state of the gas sensor. It is difficult to sense the abnormal state of the gas sensor appropriately by the conventional diagnosis method for the gas sensor.

It is an object of the present invention to provide gas sensor diagnostic or control method and/or apparatus suitable for detecting an abnormal state of a gas sensor accurately.

According to one aspect of the present invention, a gas sensor diagnostic method of diagnosing an abnormal state of a gas sensor arranged to output a sensor output value corresponding to a concentration of a specified gas component in an exhaust gas of an internal combustion engine, the gas sensor diagnostic method includes: a fuel supply detecting step of detecting an interruption of a fuel supply to the internal combustion engine, and a restart of the fuel supply after the interruption of the fuel supply; a response time period accumulating step of determining a response time period by accumulating a first time period that the sensor output value reaches from a first threshold value to a second threshold value after the detection of the interruption of the fuel supply, and a second time period that the sensor output value reaches from a third threshold value to a fourth threshold value after the detection of the restart of the fuel supply after the interruption of the fuel supply; and an abnormal state diagnosing section of determining an abnormal state of the gas sensor when the response time period is greater than a predetermined time period.

According to another aspect of the invention, a gas sensor diagnostic apparatus to diagnose an abnormal state of a gas sensor arranged to output a sensor output value corresponding to a concentration of a specified gas component in an exhaust gas of an internal combustion engine, the gas sensor diagnostic apparatus includes: a fuel supply detecting section configured to detect an interruption of a fuel supply to the internal combustion engine, and a restart of the fuel supply after the interruption of the fuel supply; a response time period accumulating section configured to determine a response time period by accumulating a first time period that the sensor output value reaches from a first threshold value to a second threshold value after the detection of the interruption of the fuel supply, and a second time period that the sensor output value reaches from a third threshold value to a fourth threshold value after the detection of the restart of the fuel supply after the interruption of the fuel supply; and an abnormal state diagnosing section configured to determine an abnormal state of the gas sensor when the response time period is greater than a predetermined time period.

DETAILED DESCRIPTION OF THE INVENTION

Figure 1:
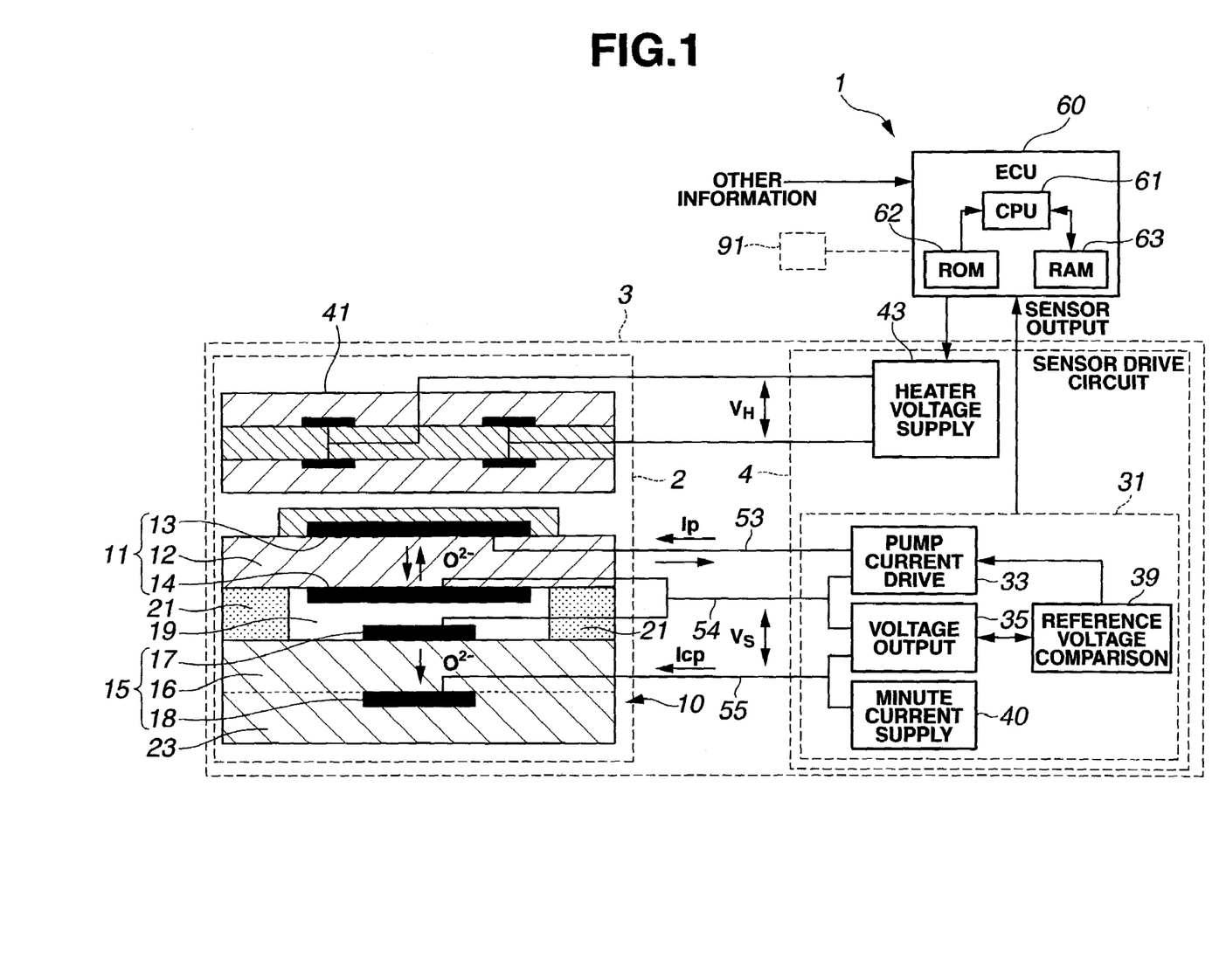
FIG. 1 is a view schematically showing a structure of a gas sensor system including a gas sensor control device 1 and a gas sensor unit 3, according to a first embodiment (and a second embodiment) of the present invention.

FIGS. 1~5 show a gas sensor diagnosis or diagnostic process for determining whether a gas sensor is in an abnormal state or not, and a gas sensor system, according to a first embodiment of the present invention. As shown in FIG. 1, the gas sensor system includes a gas sensor unit 3 and a gas sensor control unit or controller 1. In the example shown in FIG. 1, gas sensor unit 3 employs a wide-range (or full-range) air-fuel ratio sensing element 10 (hereinafter referred simply as sensing element 10) capable of sensing the oxygen concentration in a wide (or full) range of the air-fuel ratio from the rich region to the lean region across the theoretical air-fuel ratio. In this example, the gas sensor system is arranged to sense the concentration of oxygen contained in exhaust gases of an internal combustion engine for a vehicle, by gas sensor unit 3, and to use, or enable the use of, the sensed oxygen concentration for the control (such as feedback control) of the air-fuel ratio of the internal combustion engine.

Gas sensor unit 3 has the structure schematically shown in FIG. 1, and produces a sensor output value representing the oxygen concentration in the exhaust gas mixture of the internal combustion engine. Gas sensor unit 3 includes a gas sensor 2 which includes the sensing element 10 and a ceramic heater 41. Gas sensor unit 3 of this example further includes a sensor drive circuit 4 which includes a sensor control circuit 31 connected with sensing element 10, and a heater voltage supply circuit 43 connected with ceramic heater 41. Gas sensor unit 3 of FIG. 1 further includes three lead lines (or wires) 53, 54 and 55 for connecting sensing element 10 electrically with sensor control circuit 31. The three lead lines are: pump-side lead line 53, common lead line 54 and sensor-side lead line 55.

Gas sensor control device 1 has the structure schematically shown in FIG. 1. Gas sensor control device 1 includes an ECU (engine control unit) 60 for diagnosing gas sensor 2 and for controlling heater voltage supply circuit 43 in accordance with a sensor resistance signal supplied from sensor control circuit 31 separately. Gas sensor control device 1 may further include an output section 91 which is connected with ECU 60 and which includes a display or a warning device, for presenting the results of the diagnosing process according to this embodiment.

Heater voltage supply circuit 43, ECU 60 and sensor control circuit 31 start the respective operations in response to a start signal inputted from the outside at the time of a start of the internal combustion engine.

Sensing element 10 of gas sensor 2 includes a laminate of a shield layer 23, an oxygen concentration sensing cell 15, a gas sensing chamber 19 and an oxygen pumping cell 11 which are laminated in this order from bottom to top as viewed in FIG. 1.

Oxygen pumping cell 11 of sensing element 10 includes porous electrodes 13 and 14 provided, respectively, on the upper and lower sides of a solid electrolyte plate or layer 12, and performs the function of pumping oxygen (O2) as a specific gas component to be monitored by gas sensor 2. Oxygen concentration sensing cell 15 of sensing element 10 includes porous electrodes 17 and 18 provided, respectively, on the upper and lower sides of a solid electrolyte plate or layer 16, and performs the function of producing an electromotive force in accordance with the oxygen concentration. Gas sensing chamber 19 is a cavity formed between the oxygen pumping cell 11 and oxygen concentration sensing cell 15, and so arranged that measurement gas to be examined is introduced into gas sensing chamber 19. The porous electrode 14 of pumping cell 11 and the porous electrode 17 of sensing cell 15 are disposed so that both electrodes are exposed in gas sensing chamber 19, and both confront each other. A gas diffusion porous layer 21 for defining gas sensing chamber 19 between pumping cell 11 and sensing cell 15 and for controlling the diffusion rate of the gas is disposed in a path for introducing the measurement gas to be examined, into gas sensing chamber 19. In this example, the solid electrolyte plates 12 and 16, and shield layer 23 are formed by using, as a main component of material, partially stabilized zirconia including yttria as a stabilizer in a solid solution. Porous electrodes 13, 14, 17 and 18 are made predominantly of platinum.

Shield layer 23 is disposed on the (lower) side of solid electrolyte plate 16 of sensing cell 15 opposite to gas sensing chamber 19 so that the solid electrolyte plate 16 is disposed between gas sensing chamber 19 on the upper side and shield layer 23 on the lower side. The porous electrode 18 disposed between shield layer 23 and sensing cell 15 stores oxygen in pores in the electrode 18. The thus-accumulated oxygen serves as reference oxygen in oxygen concentration sensing cell 15. Therefore, porous electrode 18 can serve as a reference oxygen electrode.

Ceramic heater 41 of gas sensor 2 is shaped like a flat plate as shown in FIG. 1. Ceramic heater 41 is disposed on the upper side of oxygen pumping cell 11 so that ceramic heater 41 and oxygen pumping cell 11 confront each other. Ceramic heater 41 is a device for activating sensing element 10. Ceramic heater 41 receives the supply of electric power from heater voltage supply circuit 43, and controls the temperature of sensing element 10 to a predetermined temperature. Heater voltage supply circuit 43 supplies power to ceramic heater 41 under the control of ECU 60, as mentioned later.

Sensor control circuit 31 is electrically connected with sensing element 10 by the before-mentioned three lead lines 53, 54 and 55, as shown in FIG. 1, and arranged to deliver a sensor output to ECU 60. Sensor control circuit 31 is a circuit known per se. Sensor control circuit 31 includes a pump current drive circuit 33, a voltage output circuit 35, a reference voltage comparison circuit 39 and a minute current supply circuit 40.

Minute current supply circuit 40 of sensor control circuit 31 is to cause minute current Icp to flow from porous electrode 18 to porous electrode 17 of sensing cell 15. By the supply of minute current Icp from minute current supply circuit 40, oxygen is drawn to porous electrode 18, which functions as an oxygen reference electrode. Voltage output circuit 35 is a circuit to sense an electromotive force Vs generated between porous electrodes 17 and 18 of oxygen concentration sensing cell 15. Reference voltage comparison circuit 39 is a comparator which holds therein a predetermined reference voltage (450 [mV] in this example); compares the electromotive force Vs sensed by voltage output circuit 35 with the reference voltage; and feeds the result of the comparison back to pump current drive circuit 33. In accordance with the result of the comparison fed back from reference voltage comparison circuit 39, the pump current drive circuit 33 controls the pump current Ip supplied to oxygen pumping cell 11.

ECU 60 of gas sensor control device 1 includes CPU 61, ROM 62 and RAM 63, as shown in FIG. 1. CPU 61 is a main component of gas sensor control device 1. Specifically, CPU 61 is configured to control heater voltage supply circuit 43 controlling the supply of electricity to ceramic heater 41. ROM 62 stores programs and data such as various set values (judgment values Va, Vb and Vc) used in the later-mentioned diagnosing process. RAM 63 is a memory that can be both read and altered (written) in normal operation. ECU 60 receives the sensor output value and sensor resistance signal which are outputted from gas sensor 2 through sensor drive circuit 4. Moreover, ECU 60 receives other information such as a signal representing a condition of fuel supply to the internal combustion engine, and a signal representing the on/off condition of an ignition switch.

In the example shown in FIG. 1, the sensor control circuit 31 and heater voltage supply circuit 43 are constituent parts of gas sensor unit 3. However, it is optional to construct the gas sensor unit 3 and gas sensor control device 1 so that either or both of gas sensor control circuit 31 and heater voltage supply circuit 43 is included in gas sensor control device 1, instead of gas sensor unit 3. When, for example, gas sensor control device 1 includes both of gas sensor control circuit 31 and heater voltage supply circuit 43, and sensor unit 3 includes only the gas sensor 2, the output of gas sensor 2 is inputted directly to gas sensor control device 1. Thus, the sensor output of gas sensor 2 may be inputted to gas sensor control device 1, directly or through an interface or interfaces such as sensor control circuit 31.

Figure 2:
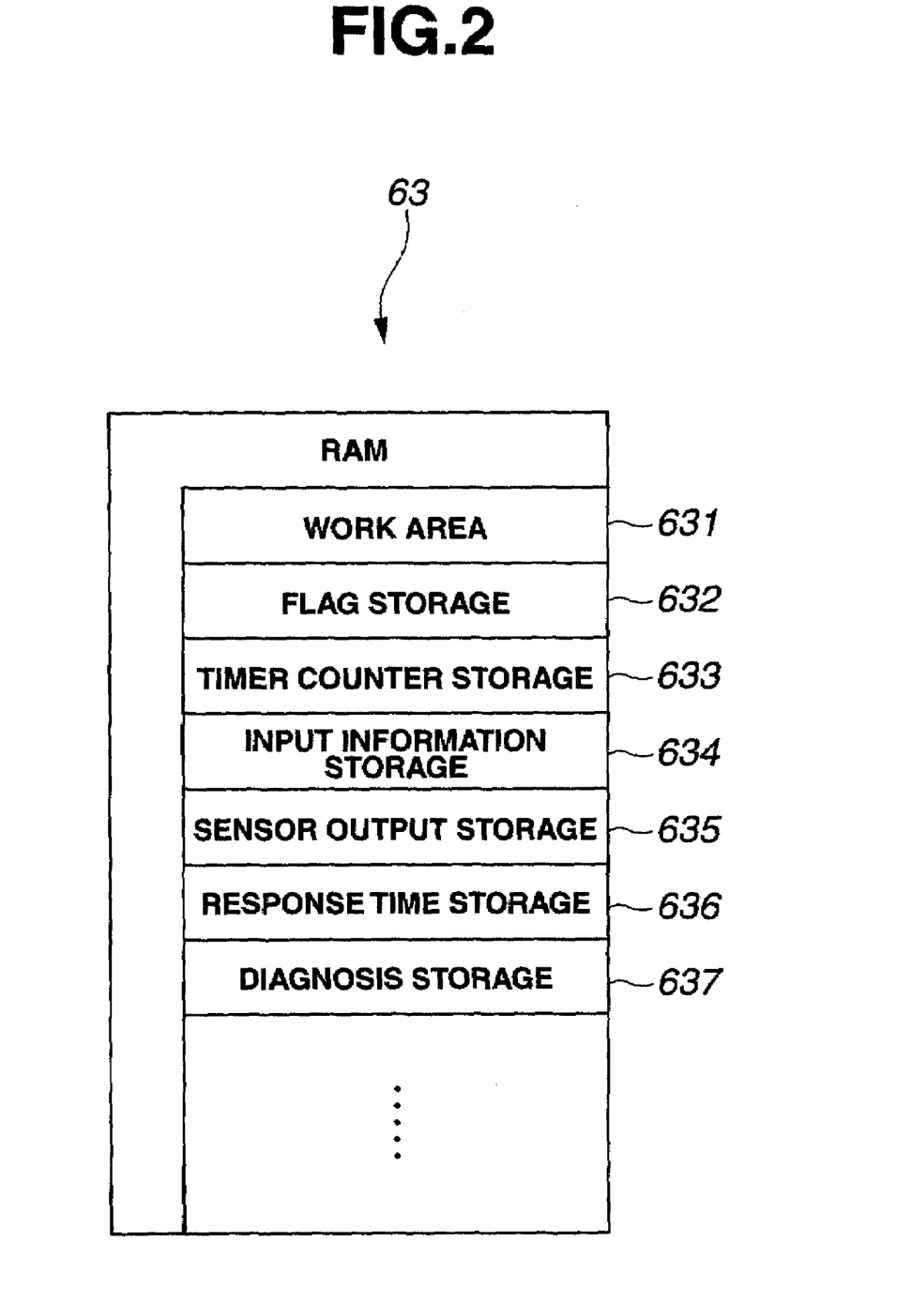
FIG. 2 is a schematic view for illustrating storage area of RAM 63 shown in FIG. 1.

FIG. 2 schematically shows memory areas in RAM 63 of ECU 60. In the example of FIG. 2, RAM 63 includes: a work area 631 for storing various programs and set values read from ROM 62 and the results of calculation performed by CPU 61; a flag storage area 632 for storing a measurement end flag indicating the execution or non-execution of the response delay diagnosis; a timer counter storage area 633 for storing a count to which a predetermined number is added at regular time intervals according to a timer program (not shown); an input information storage area 634 for storing input information supplied to gas sensor control device 1; a sensor output storage area 635 for storing the sensor output value outputted from gas sensor unit 3; a response time storage area 636 for storing a response time period T1 corresponding to a first time period, and a response time period T2 corresponding to a second time period; a diagnosis storage area 637 for storing for storing the result of the diagnosing process. RAM 63 may further include other storage areas according to the need.

Gas sensor control device 1 controls heater voltage supply circuit 43 in the following manner. Sensor control circuit 31 is arranged to deliver the sensor resistance signal to ECU 60. Though not shown in FIG. 1, sensor control circuit 31 includes a sensor resistance sensing circuit which is known per se. This sensor resistance sensing circuit is arranged to supply a current of a constant value periodically to oxygen concentration sensing cell 15 from a current supply circuit provided separately from minute current supply circuit 40; to sense, as the sensor resistance signal, a potential difference produced between the porous electrodes 17 and 18 of the oxygen concentration sensing cell 15 due to the supply of the current to sensing cell 15; and to supply the thus-obtained sensor resistance signal to ECU 60. ECU 60 determines the temperature Tc of sensing element 10 from the sensor resistance signal supplied from gas sensor unit 3, and delivers a heater control signal to control the voltage applied to ceramic heater 41, to heater voltage supply circuit 43. Specifically, in this example, ECU 60 performs a temperature control process to regulate the voltage VH applied to the heater in accordance with the sensor resistance signal supplied from sensor control circuit 31 so as to bring the temperature Tc of sensing element 10 closer to a normal temperature (800 [° C.], for example) higher than or equal to an activation temperature (600 [° C.], for example), and to bring the sensor resistance Rpvs of oxygen concentration sensing cell 15, toward a target resistance Rta corresponding to the normal temperature. The temperature Tc at oxygen concentration sensing cell 15 of sensing element 10 is related to the sensor resistance Rpvs, so that temperature Tc can be determined from the sensor resistance Rpvs. Consequently, the oxygen pumping cell 11 and oxygen concentration sensing cell 15 are heated above the activation temperature, and sensing element 10 is brought to an active state capable of sensing the oxygen. The temperature control process performed by ECU 60 is known per se. Since it is possible to employ, as the temperature control process, a control process disclosed in a published Japanese Patent Application Publication No. 2003-185626, further detailed explanation is omitted.

The sensor system determines the oxygen concentration in the exhaust gas mixture in accordance with the sensor output from gas senor unit 3, and determines the air-fuel ratio in the following manner. Between porous electrodes 17 and 18 of oxygen concentration sensing cell 15, there is produced an electromotive force Vs corresponding to the oxygen concentration in gas sensing chamber 19. So as to hold this electromotive force Vs at a constant value (450 [mV], for example), oxygen (O2) is drawn into or out of gas sensing chamber 19 in sensing element 10, with oxygen pumping cell 11. In this case, the magnitude and direction of the pump current flowing through pumping cell 11 are varied in dependence on the oxygen concentration. Therefore, the gas sensor system can sense the oxygen concentration in the exhaust gases by using the sensed pumping current Ip. In the first embodiment, the voltage proportional to the magnitude of pumping current Ip is delivered, as the sensor output, from sensor control circuit 31 to gas sensor control device 1, and ECU 60 of gas sensor control device 1 determines the oxygen concentration and diagnose the gas sensor 2 by using this sensor output. Moreover, ECU 60 determines the air-fuel ratio of the engine from the sensed oxygen concentration by utilizing a relationship between the oxygen concentration in the exhaust gases and the air-fuel ratio.

Figure 3:
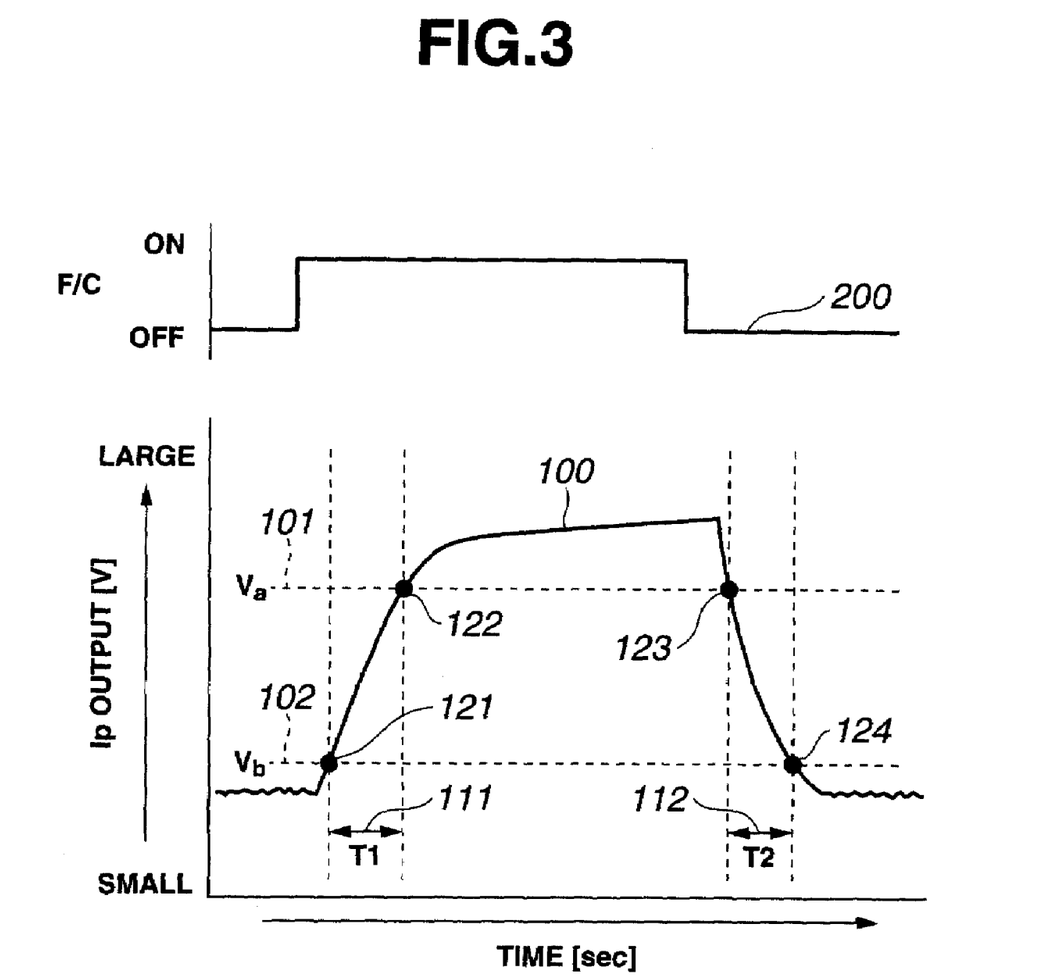
FIG. 3 is a graph showing, as an example, a sensor signal showing variation with time of sensor output value outputted from gas sensor unit 3 after a start of interruption of fuel supply (F/C) to an internal combustion engine and after a restart the fuel supply after the F/C.
Figure 4:
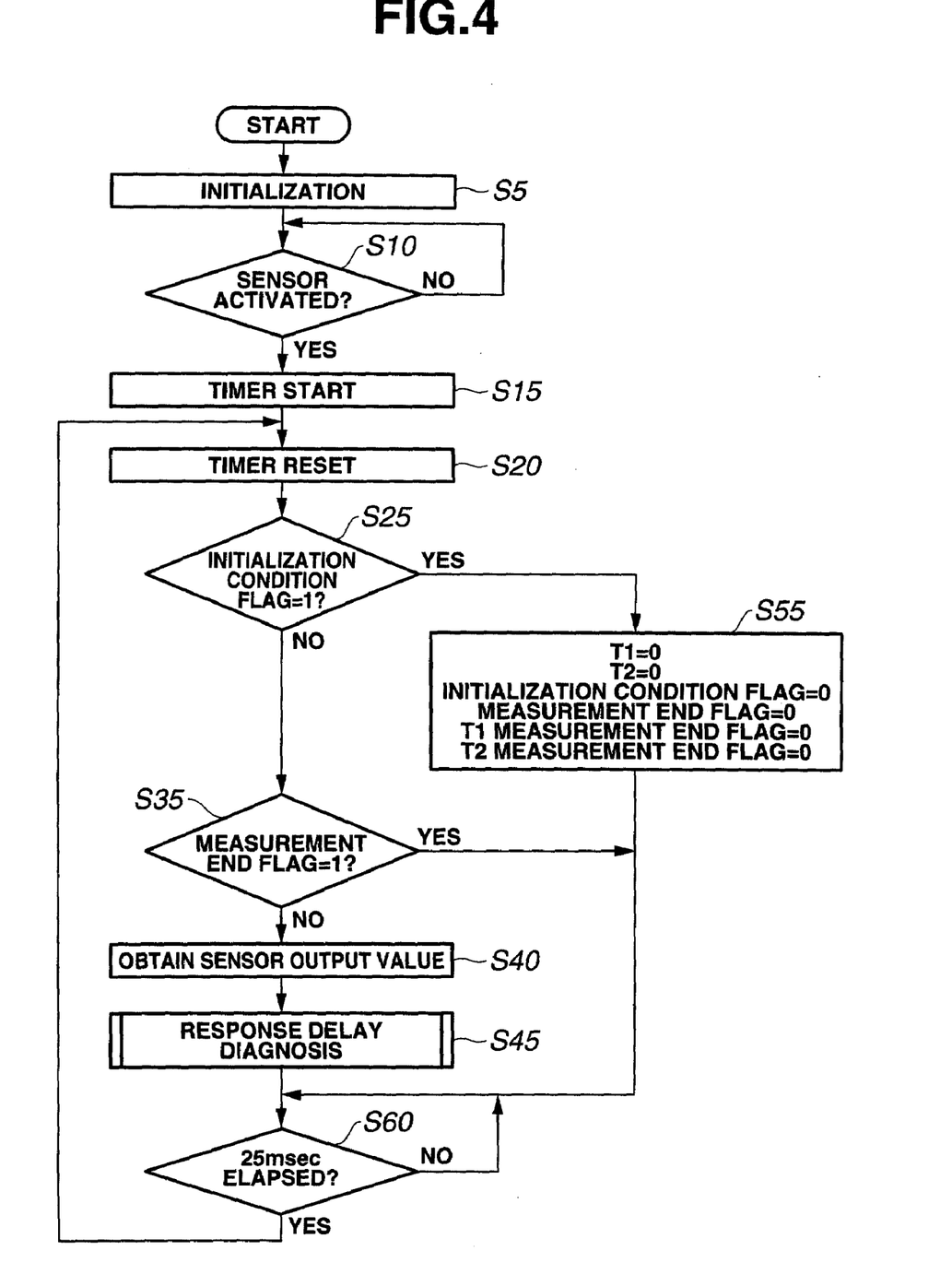
FIG. 4 is a flowchart showing a main process of a diagnostic method according to the first embodiment, for examining whether or not gas sensor 2 is in an abnormal state.
Figure 5:
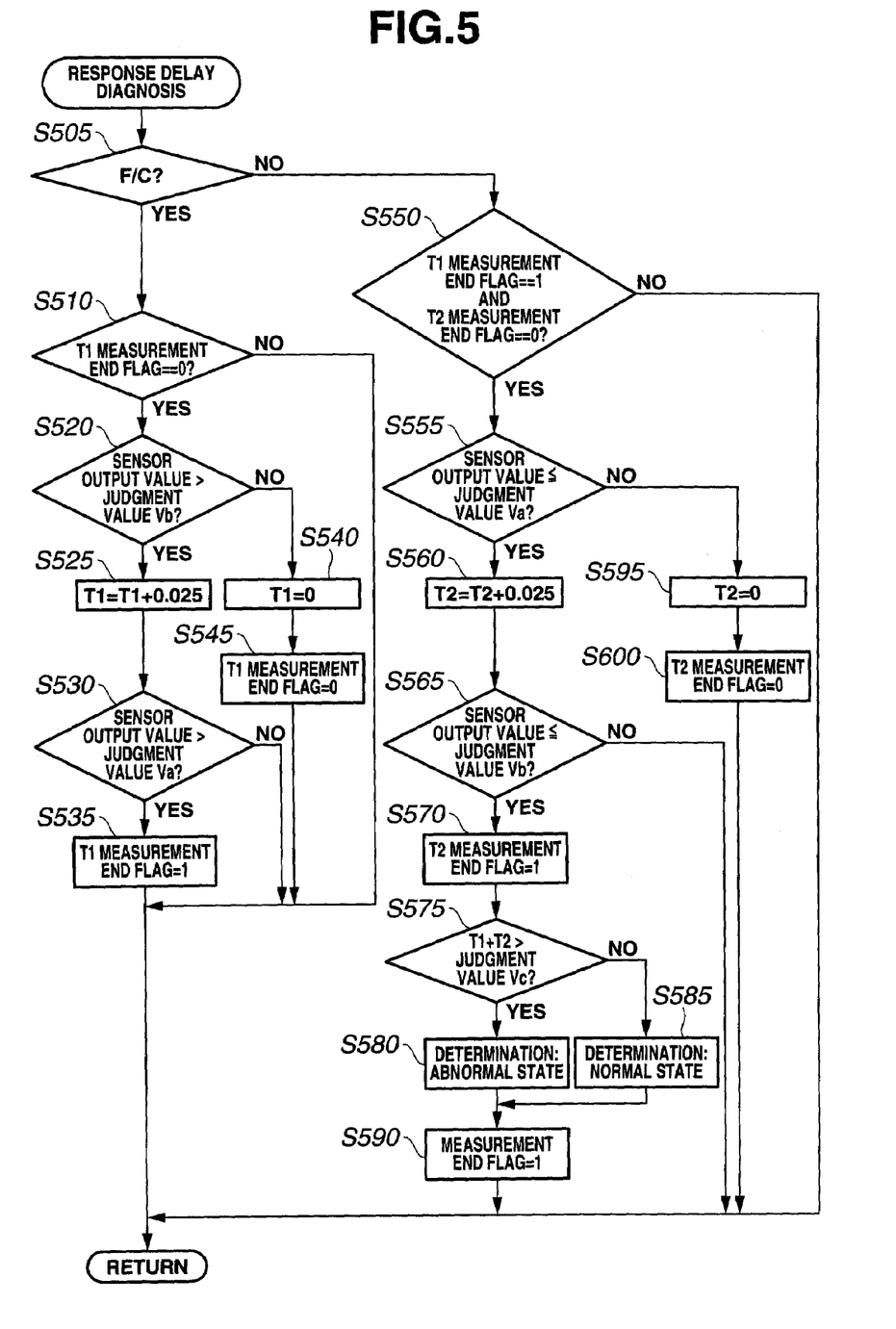
FIG. 5 is a flowchart showing a response delay diagnosis process performed in the main process of FIG. 4.

FIGS. 3~5 are views for illustrating a gas sensor diagnostic method, according to the first embodiment, of determining whether or not the gas sensor 2 is in an abnormal state, in accordance with the sensor output value of gas sensor unit 3. FIG. 3 is a graph showing, as an example, variation with time of the sensor output outputted from gas sensor unit 3 after a start of interruption (hereinafter referred as F/C) of fuel supply to the internal combustion engine and after restart of the fuel supply after the F/C. FIG. 4 is a flowchart showing a main process of the gas sensor diagnostic method of diagnosing whether or not gas sensor 2 is in the abnormal condition. FIG. 5 is a flowchart showing a response delay diagnosis process performed in the main process of FIG. 4. In this example, CPU 61 performs the processes of FIGS. 4 and 5 according to the programs stored in ROM 62.

First, the gas sensor diagnostic method will be illustrated with reference to FIG. 3 showing sensor signal 100 representing the variation with time of the sensor output value. Sensor signal 100 of FIG. 3 shows the variation with time of the sensor output value in a case in which ON/OFF of F/C is performed at the timing shown in a signal 200. As shown in this sensor signal 100, after the start of F/C at which the F/C is brought from the OFF state to the ON state, the sensor output value (Ip output [V]) is increased with the time, and then becomes a substantially constant value which is larger than a judgment value Va shown in dotted line 101. This substantially constant value which is larger than judgment value Va is a sensor output value corresponding to a known gas concentration such as atmosphere. When the F/C is brought from the ON state to the OFF state after the start of the F/C, the fuel supply is restarted, and the control operation returns to the normal air-fuel ratio feedback control. In this case, the sensor output value is decreased with the time, and then becomes a substantially constant value which is smaller than a judgment value Vb shown in a dotted line 102. This substantially constant value which is smaller than judgment value Vb is a sensor output value corresponding to the oxygen concentration in the exhaust gas. In a case in which the response to the start of the F/C or the fuel supply restart is deteriorated for the deterioration of the gas sensor 2, the time period that the sensor output value reaches the substantially constant value which is greater than judgment value Va after the start of the F/C is lengthen. In a case in which the air-fuel ratio control of the internal combustion engine is performed by this sensor output value of the gas sensor 2 with the deteriorated response, it causes problems that the harmful exhaust gas components increases. In this example, CPU 61 diagnoses whether or not gas sensor 2 is in abnormal (improper) state based on a response time period determined by accumulating a response time period T1 shown by an arrow 111 and a response time period T2 shown by an arrow 112. Response time period T1 is a time period during which the sensor output reaches from the judgment value Vb which is larger than the sensor output before the start of the F/C, to judgment value Va which is smaller than the substantially constant sensor output value corresponding to the atmosphere. Response time period T2 is a time period during which the sensor output value reaches from judgment value Va to judgment value Vb after the fuel supply restart after the start of the F/C.

FIG. 4 shows the main process of the diagnostic method according to the first embodiment. At step S5, various data and flags and so on are initialized. In this example, at step S5, CPU 61 resets a measurement end flag indicating the execution or non-execution of the response delay diagnosis process, to zero indicating that the response delay diagnosis process is not yet performed, and stores the value of the measurement end flag in flag storage area 632 of RAM 63. Furthermore, at step S5, CPU 61 clears the sensor output value stored in sensor output storage area 633. A next step S10 is for activation check for examining whether or not sensing element 10 is activated. At step S10, CPU 61 examines whether or not sensing element 10 is heated to a temperature at which the mobility of oxygen ions is sufficiently increased, and hence sensing element 10 is in an active state capable of sensing the oxygen concentration. That is, at step S10, CPU 61 examines whether or not the sensor output value is stably outputted. As explained before, there is a relationship between the temperature Tc of oxygen concentration sensing cell 15 and the sensor resistance Rpvs of oxygen concentration sensing cell 15 of sensing element 11. Therefore, CPU 61 ascertain the activation of sensing element 10 by examining the sensor resistance Rpvs of oxygen concentration sensing cell 15.

When sensing element 10 is not yet in the active state and hence the answer of step S10 is NO, CPU 61 waits until sensing element 10 is activated. When sensing element 10 is activated, CPU 61 proceeds to step S15 in response to the affirmative answer of step S10, and starts the timer at step S15, to measure time to obtain or sample values of the sensor output value periodically. This operation is to start the timer whose count is stored in timer counter storage area 633 and updated periodically by another program performed separately. At a next step S20, the count of the timer is reset and stored in timer counter storage area 633. This resetting operation is to reset the timer to measure an elapsed time from the time of timer reset to execution of a step S60. When sensing element 10 is activated, ECU 60 further starts a drive control of sensing element 10 with sensor control circuit 31.

At step S25 following step S20, CPU 61 checks or refers to flag storage area 632 of RAM 63, and judges or examines whether or not the initialization condition flag is 1. The value of the initialization condition flag is set by another program. For example, in a case in which gas sensor 2 is attached to the internal combustion engine of the vehicle, the ON/OFF of the ignition switch is monitored. When the stop of the internal combustion engine is sensed, the initialization condition flag is set to one. By this operation, it is possible to perform the diagnostic process only once each time the ignition switch is turned on. When the initialization condition flag is one, and hence the answer of step S25 is YES, CPU 61 proceeds to a step S55. At step S55, response time period T1 and response time period T2 are set to zero, and stored in response time storage area 636. Moreover, at step S55, the initialization condition flag, a measurement end flag, a response time period T1 measurement end flag, and a response time period T2 measurement end flag are set to zero, and stored in flag storage area 632. This step S55 is to make setting to perform the diagnostic progress. Subsequently to step S55, CPU 61 proceeds to a step S60 described later.

When the initialization condition flag is zero and hence the answer of step S25 is NO, CPU 61 checks flag storage area 632, and examines or judges whether or not the measurement end flag is one at step S35. When the measurement end flag is one indicating the execution of the response delay diagnosis process, and hence the answer of step S35 is YES, CPU 61 proceeds to step S60. When the measurement end flag is zero indicating the non-execution of the response delay diagnosis process, and hence the answer of step S35 is NO, the sensor output value outputted from gas sensor unit 3 is obtained, and stored in sensor output storage area 635 at step S40. This sensor output value is referred by the response delay diagnosis process performed at step S45. Next, at step S45, CPU 61 performs the response delay diagnosis process for diagnosing whether or not gas sensor 2 is in the abnormal state. This response delay diagnosis process will be illustrated later with reference to the flowchart of FIG. 5.

At step S60 following step S45 and step S55, CPU 61 checks timer counter storage area 633, and judges whether or not 25 [msec] has elapsed from the timer reset operation at step S20. By this operation, the sensor output value is obtained at regular time intervals of a predetermined time period (25 [msec] in this embodiment). This predetermined time period may be arbitrarily set by the characteristic, the use and so on of gas sensor 2. The predetermined time period is not limited to 25 [msec] in this embodiment. When 25 [msec] has not elapsed and hence the answer of step S60 is NO, CPU 61 waits until 25 [msec] has elapsed. When 25 [msec] has elapsed and hence the answer of step S60 is YES, CPU 61 returns to step S20.

As mentioned above, the main process of the abnormal state diagnosis process of gas sensor control device 1 is performed. FIG. 5 shows, in the form of the flowchart, the response delay diagnosis process performed in the main process of FIG. 4. At step S505, CPU 61 checks or refers to input information storage area 634, and judges whether or not it is during the F/C. Step S505 can serve as a fuel supply detecting step of sensing the F/C start and the fuel supply restart after the F/C. The operation when it is not during the F/C and the answer of step S505 is NO will be illustrated later. When it is during the F/C and the answer of step S505 is YES, CPU 61 checks flag storage area 632, and examines whether or not the response time T1 measurement end flag is zero at step S510. This operation judges whether or not the measurement of the response time T1 is finished. When the response time T1 measurement end flag is one indicating the completion of the measurement of the response time T1, and hence the answer of step S510 is NO, the response delay diagnosis process is finished, and CPU 61 returns to the main process shown in FIG. 4.

When the response time T1 measurement end flag is zero indicating the non-completion of the measurement of response time T1, and hence the answer of step S510 is YES, then CPU 61 proceeds to step S520. At step S520, CPU 61 checks sensor output storage area 635, and judges whether or not the sensor output value obtained at step S40 is greater than judgment value Vb. Judgment value Vb of step S520 corresponds to a first threshold value. Judgment value Vb is arbitrarily set in accordance with operating conditions and so on of the internal combustion engine. For example, this judgment value Vb is set to 2.5 [V].

When the sensor output value is equal to or lower than judgment value Vb, and hence the answer of step S520 is NO, response time period T1 is set to zero, and stored in response time storage area 636 at step S540. In this way, when the sensor output value is not continuously greater than judgment value Vb (S520:NO), response time period T1 is reset at step S540. Accordingly, it is possible to appropriately response time period T1 without the influence of the improper sensor output value with the accidental noise and so on. At step S545 following step S540, the response time T1 measurement end flag is set to zero, and stored in flag storage area 632. Subsequently to step S545, the response delay diagnosis process is finished, CPU 61 returns to the main process shown in FIG. 4.

When the sensor output value is greater than judgment value Vb and hence the answer of step S520 is YES, CPU 61 proceeds to step S525. At step S525, an obtaining time interval of the sensor output value (0.025 [sec] in this embodiment) is added to response time period T1, and response time period T1 is stored in response time storage area 636. This step S525 together with step S560 and step S575 can serve as a response time accumulating step of accumulating the time period (response time period T1 corresponding to the first time period) that the sensor output value after the start of the F/C reaches from judgment value Vb to judgment value Va.

At step S530 following step S525, CPU 61 judges or examines whether or not the sensor output value is greater than judgment value Va. This judgment value Va of step S530 corresponds to a second threshold value. Judgment value Va is set to an arbitrary value greater than judgment value Vb of step S520 in accordance with the operating conditions and so on of the internal combustion engine. For example, judgment value Va is set to 3.0 [V]. When the sensor output value is equal to or lower than judgment value Va, and hence the answer of step S530 is NO, the response delay diagnosis process is finished, and CPU 61 returns to the main process of FIG. 4. When the sensor output value is greater than judgment value Va, and hence the answer of step S530 is YES, then CPU 61 proceeds to step S535. At step S535, the response time T1 measurement end flag is set to one, and stored in flag storage area 632. By this operation, it is possible to obtain response time period T1 required for the sensor output value after the detection of the F/C (S505:YES) to reach from judgment value Vb (S520:YES) to judgment value Va (S530:YES). In the sensor signal 100 of FIG. 3, response time period T1 is shown by an arrow 111 representing a time period during which the sensor output values from sensor output value 121 to sensor output value 122 are obtained.

When it is not during the F/C and hence the answer of step S505 is NO, CPU 61 checks flag storage area 632, and examines whether or not the response time period T1 measurement end flag is one and the response time period T2 measurement end flag is zero at step S550. By this operation, response time period T2 is measured in a case in which the measurement of the response time period T1 is completed and the measurement of the response time period T2 is not completed (S550: Yes). When the answer of step S550 is NO, the response delay diagnosis process is finished, and CPU 61 returns to the main process shown in FIG. 4. When the answer of step S550 is YES, CPU 61 judges whether or not the sensor output value is equal to or lower than judgment value Va at step S555. Judgment value Va of step S555 corresponds to a third threshold value. This judgment value Va is arbitrarily set in accordance with the operating conditions and of the internal combustion engine. In this embodiment, judgment value Va used as the third threshold value is identical to judgment value Va of step S530. However, it is optional to set the judgment value of step S555 to a value different from the judgment value of step S530.

At step S555, when the sensor output value is greater than judgment value Va, and hence the answer of step S555 is NO, response time period T2 is set to zero, and stored in response time storage area 636 at step S595. In this way, when the sensor output value is not continuously equal to or lower than judgment value Va (S555:NO), response time period T2 is reset at step S595. Accordingly, it is possible to obtain appropriately response time period T2 without the influence of the improper sensor output value with the accidental noise and so on. At step S600 following step S595, the response time T2 measurement end flag is set to zero, and stored in flag storage area 632.

When the sensor output value is equal to or lower than judgment value Va and hence the answer of step S555 is YES, CPU 61 proceeds to step S560. At step S560, an obtaining time interval of the sensor output value (0.025 [sec] in this embodiment) is added to response time period T2, and response time period T2 is stored in response time storage area 636. This step S560 together with step S525 and step S575 can serve as a response time accumulating step of accumulating the time period (response time period T2) that the sensor output value reaches from judgment value Va to judgment value Vb after the detection of the fuel supply restart after the F/C. At step S565 following step S560, CPU 61 judges whether or not the sensor output value is equal to or lower than judgment value Vb. Judgment value Vb of step S565 corresponds to a fourth threshold value. This judgment value Vb is arbitrarily set in accordance with the operating conditions and of the internal combustion engine. In this embodiment, judgment value Vb used as the fourth threshold value is identical to judgment value Vb of step S520. However, it is optional to set the judgment value of step S565 to a value different from the judgment value of step S520.

When the sensor output value is greater than judgment value Vb, and hence the answer of step S565 is NO, the response delay diagnosis process is finished, and CPU 61 returns to the main process of FIG. 4. When the sensor output value is equal to or lower than judgment value Vb, and hence the answer of step S565 is YES, then CPU 61 proceeds to step S570. At step S570, the response time T2 measurement end flag is set to one, and stored in flag storage area 632. By this operation, it is possible to obtain response time period T2 required for the sensor output value after the detection of the fuel supply restart after the F/C to reach from judgment value Va to judgment value Vb, in the case in which the measurement of response time period T1 is finished and the measurement of response time period T2 is not finished (S550:YES). In the sensor signal 100 of FIG. 3, response time period T2 is shown by an arrow 112 representing a time period during which the sensor output values from sensor output value 123 to sensor output value 124 are obtained.

At step S575 following step S570, CPU 61 judges whether or not the accumulation value of response time period T1 and response time period T2 is greater than judgment value Vc. This operation of accumulating response time period T1 and response time period T2, and the operations of step S525 and step S560 corresponds to a response time period accumulating step. Judgment value Vc is an arbitrary value set in accordance with the characteristics and so on of gas sensor 2. For example, this judgment value Vc is set to 4.0 [sec]. When the accumulation value of response time period T1 and response time period T2 is greater than judgment value Vc, and hence the answer of step S575 is YES, CPU 61 determines that gas sensor 2 is in the abnormal state, and the diagnosis result is stored in diagnosis storage area 637 at step S580. When the accumulation value of response time period T1 and response time period T2 is equal to or lower than judgment value Vc, and hence the answer of step S575 is NO, CPU 61 determines that gas sensor 2 is in the normal state, and the diagnosis result is stored in diagnosis storage area 637 at step S585. Step S575, step S580 and step S585 correspond to an abnormal state diagnosing step. At step S590 following step S580 or step S585, the measurement end flag is set to one that represents the response delay diagnosis process is executed, and stored in flag storage area 632. Next, the response delay diagnosis process is finished, and CPU 61 returns to the main process shown in FIG. 4.

The diagnostic system according to the first embodiment performs the response delay diagnostic process in this way. The diagnostic system may be arranged to notify the user, of the result of the diagnosis by audible or visible message with the output device 91 including a device such as a display, a warning device or lamp, or a speaker, or may be arranged to supply the result of the diagnosis to external equipment through an output terminal for the diagnosis, or by serial communication.

CPU 61 of FIG. 1 is configured to sense the F/C and the fuel supply restart after the F/C at step S505 in the flowchart shown in FIG. 5. CPU 61 can serve as a fuel supply detecting section. CPU 61 of FIG. 1 is configured to determine the response time period (S525, S560, S575) by accumulating or summing response time period T1 required for the sensor output value after the detection of the start of the F/C to reach from judgment value Vb corresponding to the first threshold value (S520:Yes) to judgment value Va corresponding to the second threshold value (S530:Yes), and response time period T2 required for the sensor output value after the detection of the fuel supply restart after the F/C to reach from judgment value Va corresponding to the third threshold value (S555: Yes) to judgment value Vb corresponding to the fourth threshold value (S565:Yes). CPU 61 can serve as a response time period accumulating section. CPU 61 is configured to determine that the gas sensor is in the abnormal state (S580) when the response time period obtained by accumulating response time period T1 and response time period T2 is greater than judgment value Vc (S575:YES). CPU 61 corresponds to an abnormal state diagnosing section.

As mentioned above, gas sensor control device 1 according to the first embodiment is configured to diagnose whether or not gas sensor 2 is in the abnormal or improper state by using the response time period obtained by accumulating response time period T1 required for the sensor output value after the F/C to reach from judgment value Vb corresponding to the first threshold value to judgment value Va corresponding to the second threshold value, and response time period T2 required for the sensor output value after the fuel supply restart after the F/C to reach from judgment value Va corresponding to the third threshold value to judgment value Vb corresponding to the fourth threshold value (S575, S580 and S585). Accordingly, it is possible to sense the abnormal state of gas sensor 2 accurately, relative to a case of judging whether or not the gas sensor is in the abnormal state by using only either response time period T1 or response time period T2. By this gas sensor control device 1, it is possible to sense the abnormal state of the gas sensor accurately, even in a case in which the internal combustion engine is controlled on the lean side. Moreover, it is possible to enlarge difference between the variations of the sensor output values in the normal state and in the abnormal state (deterioration state) by using response time period T1 and response time period T2. Accordingly, it is possible to readily set judgment value Vc serving as the threshold value for diagnosing whether or not gas sensor 2 is in the abnormal state, and to accurately perform the abnormal state diagnosis of the gas sensor by using this judgment value Vc. By gas sensor control device 1 according to the first embodiment, it is possible to appropriately detect the time degradation such as the clogging of the gas through holes (not shown) of the protector of gas sensor 2, and the porous portions (for example, gas diffusion porous layer 21) which introduces the exhaust gas into sensing element 10.

Figure 6:
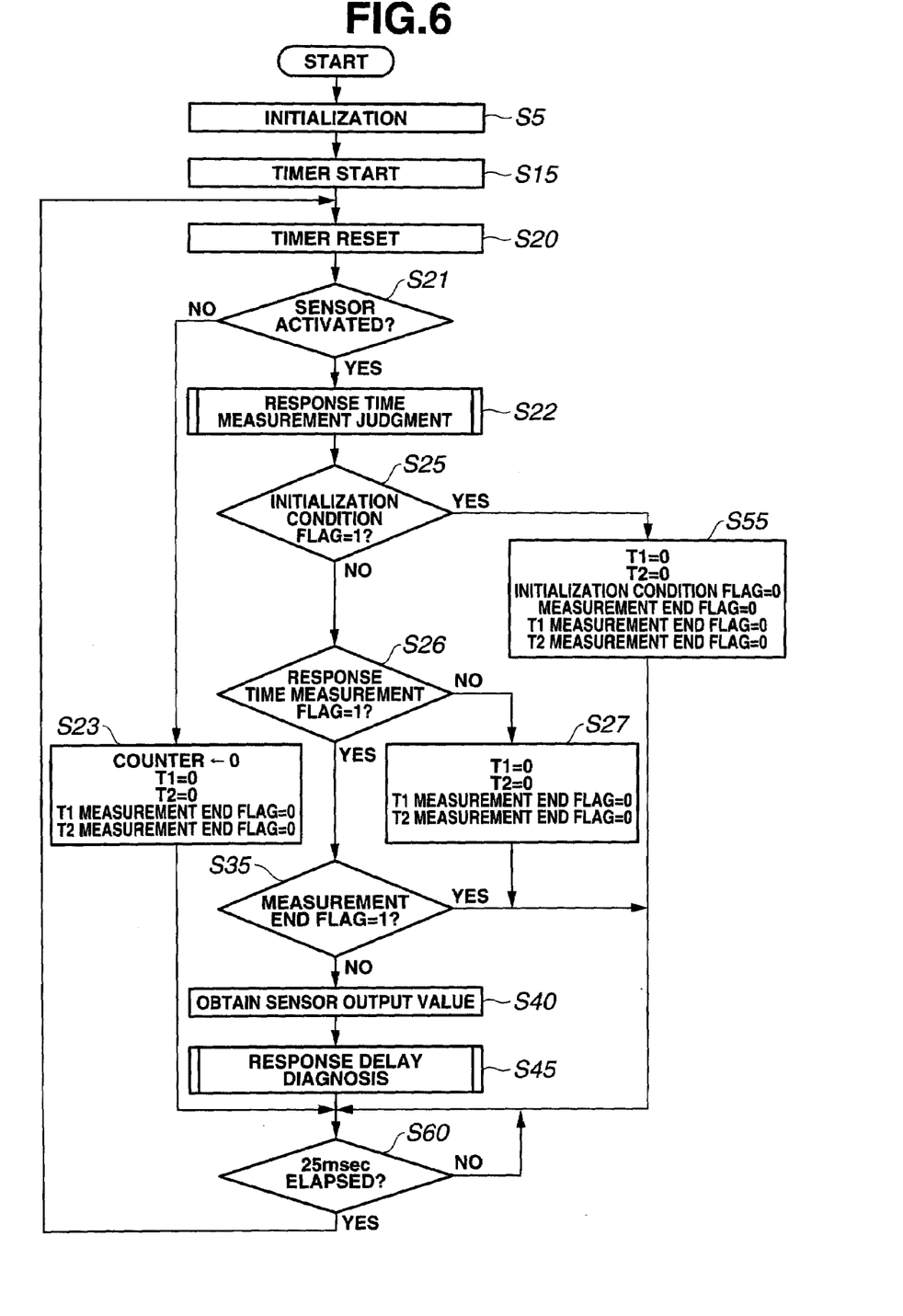
FIG. 6 is a flowchart showing a main process of a diagnostic method according to the second embodiment, for examining whether or not the gas sensor 2 is in an abnormal condition.
Figure 7:
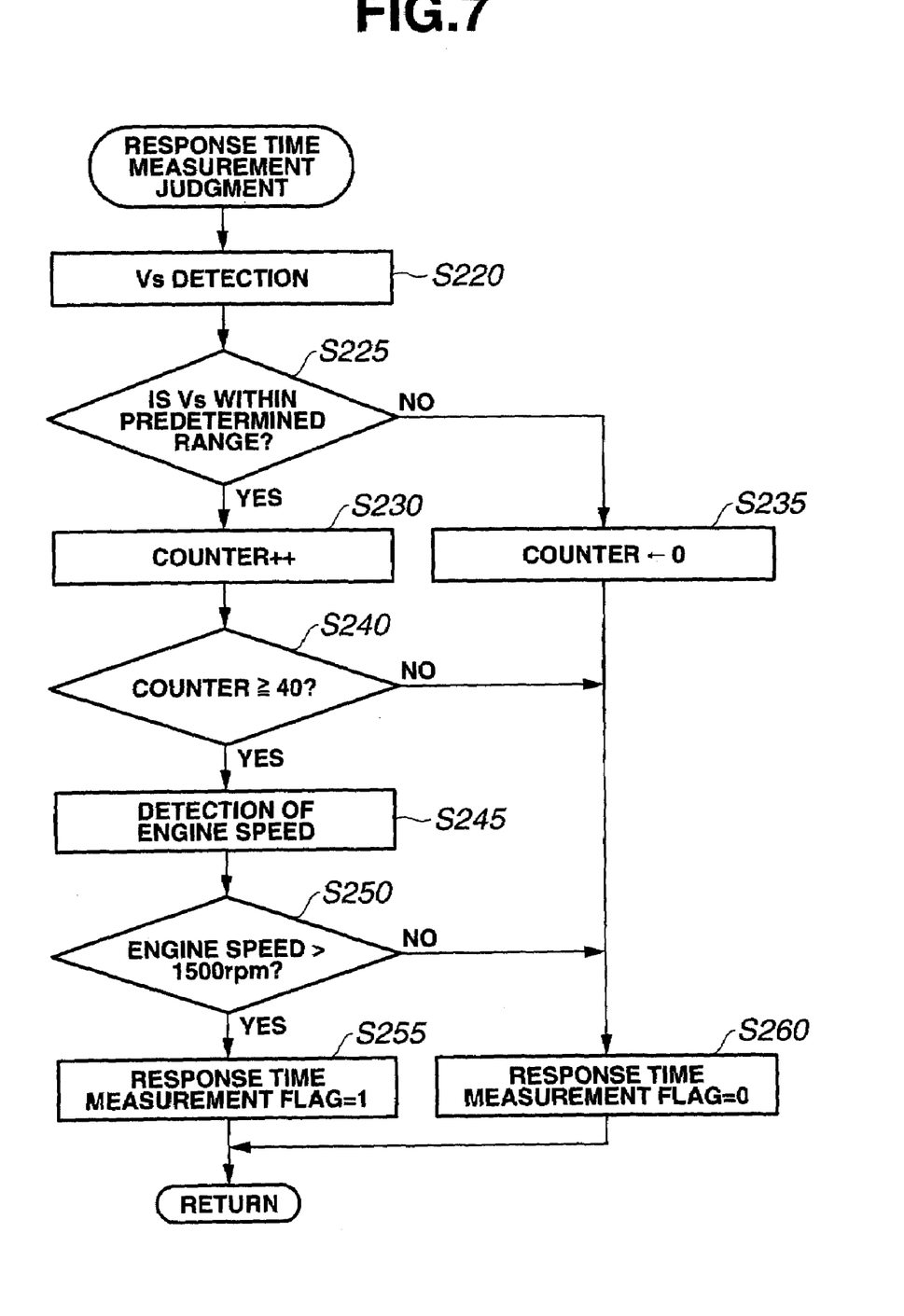
FIG. 7 is a flowchart showing a response time measurement judgment process performed in the main process of FIG. 6.

FIGS. 6 and 7 show a diagnostic method according to a second embodiment of the present invention. The diagnostic method according to the second embodiment is so configured as not to perform the response delay diagnosis process when a predetermined condition is satisfied. The gas sensor system according to the second embodiment is substantially identical in structure to the system shown in FIG. 1, so that repetitive explanation is omitted. FIG. 6 is a flowchart showing a main process of the gas sensor diagnostic method for diagnosing whether or not gas sensor 2 is in the abnormal state. FIG. 7 is a flowchart showing a response time measurement judgment process performed in the main process of FIG. 6. In this example, CPU 61 performs the processes of FIGS. 6 and 7 according to the programs stored in ROM 62. The main process of FIG. 6 includes steps substantially identical to steps shown in FIG. 4. Therefore, these steps are given the same step numbers and their detailed explanation is omitted or simplified.

As shown in the flowchart of FIG. 6, the main process of the diagnostic method according to the second embodiment does not include the operation of step S10. Unlike the main process of the diagnostic method according to the first embodiment, the main process according to the second embodiment includes operations of step S21, step S22, step S23, step S26 and step S27.

At step S5, the initialization operation is performed, and then the timer starts at step S15. Subsequently to step S15, the count of the timer is reset at step S20. At step S21, CPU 61 judges whether or not sensor element 10 is activated. This operation is identical to the operation of step S10 of the flowchart of FIG. 4 of the first embodiment. This operation corresponds to a sensor output value judging step and a diagnosis execution controlling step. When sensor element 10 is not activated and hence the answer of step S21 is NO, the response delay diagnosis process (S45) is not performed. At step S23, the counter is set to zero, and stored in work area 631 of RAM 63. This counter is a variable to store number of determination that voltage Vs generated between porous electrodes 17 and 18 of oxygen concentration sensing cell 15 is continuously within a predetermined range. The counter is set in accordance with voltage Vs in a response time measurement judgment process (step S22) described later. At step S23, the counter is set to zero, and accordingly the number that voltage Vs is continuously within the predetermined range is reset. Moreover, at step S23, response time period T1 and response time period T2 are reset to zero, and stored in response time storage area 636. Furthermore, at step S23, the response time period T1 measurement end flag and the response time period T2 measurement end flag are set to zero, and stored in flag storage area 632.

When sensing element 10 is activated and hence the answer of step S21 is YES, the response time measurement judgment process is performed at step S22. The response time measurement judgment process is a process for judging whether or not predetermined conditions to perform the response delay diagnosis process (step S45) are satisfied. This response time measurement judgment process will be illustrated below with reference to the flowchart of FIG. 7. At step S220, voltage Vs sensed through voltage output circuit 35 and inputted to ECU 60 is sensed. At step S225 following step S220, CPU 61 checks work area 631, and judges whether or not voltage Vs sensed at step S220 is within a predetermined range (for example, 250 [mV]≦Vs≦750 [mV]). This predetermined range is arbitrarily set in accordance with the characteristics and the use of gas sensor 2, and stored in ROM 62. When voltage Vs is not within the predetermined range and hence the answer of step S225 is NO, the counter is set to zero, and stored in work area 631 at step S235. The response time period measurement flag indicating whether or not the response delay diagnosis process (step S45) is ready is set to zero indicating that the response delay diagnosis process is not ready, and stored in flag storage area 632 at step S260. Next, CPU 61 returns to the main process of FIG. 6.

When voltage Vs is within the predetermined range and hence the answer of step S225 is YES, CPU 61 increments (increases by one) the counter, and stores the counter in work area 631 at step S230. At step S240 following step S230, CPU 61 judges whether or not the counter set at step S230 is equal to or greater than the predetermined number. This step S240, step S225, step S230, step S235, and step S23 of FIG. 6 correspond to a sensor output value judging step. In this second embodiment, when voltage Vs is continuously within the predetermined range the predetermined number times, CPU 61 determines that the sensor output value is stably outputted. The predetermined number used by the operation at step S240 is appropriately set in accordance with execution interval of the main process, the characteristics and the use of gas sensor 2, and stored in ROM 62. Gas sensor 2 according to the second embodiment has a characteristic that gas sensor 2 is in a state to stably output the sensor output value when voltage Vs is continuously within the predetermined range during 1 [sec]. Therefore, the predetermined number is set to 40 in consideration of 25 [msec] of the execution interval of the main process.

When the counter is equal to or greater than 40 and hence the answer of step S240 is YES, CPU 61 checks input information storage area 634, and an engine speed or rotational speed of the internal combustion engine is sensed at step S245. This operation corresponds to an engine speed obtaining step. In this second embodiment, the engine speed of the internal combustion engine is inputted to ECU 60 at regular time intervals, and stored in input information storage area 634. Accordingly, CPU 61 checks input information storage area 634, and judges whether or not the engine speed of the internal combustion engine which is sensed at step S245 is greater than a low engine speed judgment threshold value at step S250. By this operation, the response delay diagnosis process (step S45 of FIG. 6) is not performed when the engine speed of the internal combustion engine is equal to or lower than the low engine speed judgment threshold value. This low engine speed judgment threshold value is arbitrarily set in accordance with the engine speed of the internal combustion engine at which the concentration of the specified gas component in the exhaust gas is stable, and the accuracy of the abnormal state diagnosis and so on. In this second embodiment, the low engine speed judgment threshold value is 1500 rpm. When the engine speed of the internal combustion engine is greater than 1500 rpm and hence the answer of step S250 is YES, the response time measurement flag representing whether or not the response delay diagnosis process (step S45 of FIG. 6) is ready is set to one representing that the response delay diagnosis process is ready, and stored in flag storage area 632 at step S255. Next, CPU 61 returns to the main process of the abnormal state diagnosis process.

When the counter is not equal to or greater than 40 and hence the answer of step S240 is NO, or when the engine speed of the internal combustion engine is not greater than 1500 rpm and hence the answer of step S250 is NO, the response time measurement flag is set to zero representing that the response delay diagnosis process (step S45 of FIG. 6) is not ready, and stored in flag storage area 632 at step S260. Next, CPU 61 returns to the main process of the abnormal state diagnosis process of FIG. 6.

Subsequently to the response time period measurement judgment process of step S22 of the main process, CPU 61 checks flag storage area 632, and judges whether or not the initialization condition flag is one at step S25. When the initialization condition flag is one and hence the answer of step S25 is YES, CPU 61 performs the operations of step S55 and step S60 as in the first embodiment.

When the initialization condition flag is not one and hence the answer of step S25 is NO, CPU 61 checks flag storage area 632, and judges whether or not the response time measurement flag is one at step S26. This operation corresponds to the diagnosis execution controlling step. When the response time measurement flag is not one and hence the answer of step S26 is NO, the response delay diagnosis process (step S45) is not performed. In the second embodiment, when the response time measurement flag is one, and hence the answer of step S26 is YES, the response delay diagnosis process (step S45) is performed. When the response time measurement flag is set to one at step S255 of the flowchart of FIG. 7, the operation of step S35 is performed as in the first embodiment. When the response time measurement flag is set to zero at step S260 of the flowchart of FIG. 7, the response delay diagnosis process (step S45) is not performed. Response time period T1 and response time period T2 are set to zero, and stored in response time storage area 636 at step S27. The response time period T1 measurement end flag and the response time period T2 measurement end flag are set to zero, and stored in flag storage area 632 at step S27. CPU 61 performs the operation of step S60 as in the first embodiment. The operations of step S35, step S40, step S45 and step S60 are identical to the operations in the first embodiment, and the illustration is omitted.

As described above, the abnormal state diagnostic process of the second embodiment is performed. CPU 61 of FIG. 1 is configured to obtain the engine speed of the internal combustion engine by referring to the input information storage area 634 at step S245 of the flowchart of FIG. 7. CPU 61 corresponds to an engine speed obtaining section. CPU 61 of FIG. 1 is configured to judge whether or not the sensor output value is stably outputted by judging whether or not sensing element 10 is activated at step S21 of FIG. 6. CPU 61 of FIG. 1 corresponds to a sensor output value judging section. CPU 61 of FIG. 1 is configured to accumulate the number that voltage Vs is continuously in the predetermined range by using the counter at step S225, step S230 and step S235 of the flowchart of FIG. 7 and step S23 of the flowchart of FIG. 6. CPU 61 is configured to judge whether or not the counter is equal to or greater than 40 at step S240 of the flowchart of FIG. 7, that is, to judge whether or not voltage Vs is continuously in the predetermined range during the time period of 1 [sec], and thereby to judge whether or not the sensor output value is stably outputted. CPU 61 corresponds to the sensor output value judging section. When voltage Vs is not in the predetermined range and hence the answer of step S225 is NO, and when the counter is lower than 40 and hence the answer of step S240 is NO, CPU 61 of FIG. 1 is configured to set the response time measurement flag to zero at step S260, and to control so as not to perform the response delay diagnosis process (S45) at step S26 of the flowchart of FIG. 6 (S26:NO). CPU 61 corresponds to the diagnosis execution controlling section. When CPU 61 determines that sensing element 10 is not activated and hence the answer of step S21 is NO, CPU 61 is so configured as not to perform the response delay diagnosis process (S45). CPU 61 corresponds to the diagnosis execution controlling section. When the engine speed of the internal combustion engine obtained at step S245 is equal to or lower than the low engine speed judgment threshold value, and hence the answer of step S250 is NO, CPU 61 is configured to set the response time measurement flag to zero at step S260, and to control so as not to perform the response delay diagnosis process (S45) at step S26 of the flowchart of FIG. 6. CPU 61 corresponds to the diagnosis execution controlling section.

In gas sensor control device 1 according to the second embodiment, when the engine speed of the internal combustion engine is equal to or lower than the low engine speed judgment threshold value (S250:NO), CPU 61 is configured to control so as not to perform the response delay diagnosis process (S26:No). Accordingly, the abnormal state diagnosis of gas sensor 2 is performed by using the sensor output value when the specified gas component in the exhaust gas from the internal combustion engine is stable, and it is possible to improve the accuracy of the abnormal state diagnosis. Moreover, the response delay diagnosis process (S45) is not performed when the sensor is not activated (S21:NO). When the sensor output value is not continuously in the predetermined range during the time period of 1 [sec] (S225:NO and S240: NO), and the sensor output value is not stably outputted, the response delay diagnosis operation (S45) is not performed (S26:NO). Therefore, the abnormal state diagnosis process is not performed during the time period during which the sensor output value is not stably outputted, and it is possible to improve the accuracy of the abnormal state diagnosis.

The present invention is not limited to the concrete examples of the first and second embodiments. Various modifications and variations are possible within purview of the present invention. In the above-mentioned embodiments, gas sensors 2 are configured to sense the oxygen as the specified gas in the exhaust gas, and the abnormal state diagnosis of gas sensor 2 is performed. However, gas sensor 2 is not limited to the gas sensor configured to sense the oxygen concentration as the specified gas component. For example, it is optional to employ gas sensors configured to sense concentrations of HC, CO and NOx as the specified gas components.

In the response delay diagnosis process of FIG. 5, response time period T1 and response time period T2 are used. At step S525, response time period T1 is accumulated. At step S560, response time period T2 is accumulated. In this way, response time period T1 and response time period T2 are individually accumulated. However, it is possible to obtain the response time period without individually accumulating response time period T1 and response time period T2, for obtaining the accumulation value of response time period T1 and response time period T2 which is used as the response time period for the gas sensor diagnosis.

In the above-mentioned example, the gas sensor diagnostic process is performed only one each time the ignition switch is turned on. However, the invention is not limited to this. It is possible to perform the abnormal state diagnosis process two or more times during the time period during which the ignition switch is brought from the ON state to the OFF state. In the case in which the multiple abnormal state diagnosis processes are performed, it is optional to determine the abnormal state when the accumulation value (the response time period) of response time period T1 and response time period T2 becomes greater than judgment value Vc once, or when the number that the response time period is greater than judgment value Vc reaches more than one predetermined number.

In the second embodiment, when sensing element 10 is not activated (S21:NO), when voltage Vs is not continuously in the predetermined range during 1 [sec] (S225:NO and S240: NO), and when the engine speed of the internal combustion engine is equal to or lower than the low engine speed judgment threshold value (S250:NO), the response delay diagnosis process is not performed. However, the conditions are not limited to these three conditions. It is optional to employ one or two of these three conditions. In the case in which the response delay diagnosis process is not performed when the sensor output value is not stably outputted, it is optional to sense that the predetermined conditions are satisfied, by judging whether or not a predetermined time period has elapsed after sensing element 10 is activated (S21:Yes).

In the second embodiment, the response delay diagnosis process (S45) of the flowchart of FIG. 6 is not performed when the predetermined conditions are satisfied. It is necessary that the abnormal state diagnosis process is not performed when the predetermined conditions are satisfied, and the control operation is not limited to the operation of the second embodiment. For example, it is possible that the operations of step S575~step S590 of FIG. 5 are not performed when the predetermined condition is satisfied. Moreover, it is optional to omit the diagnosis execution controlling process when the gas sensor is used under the stable state of the concentration of the specified gas component.

Figure 8:
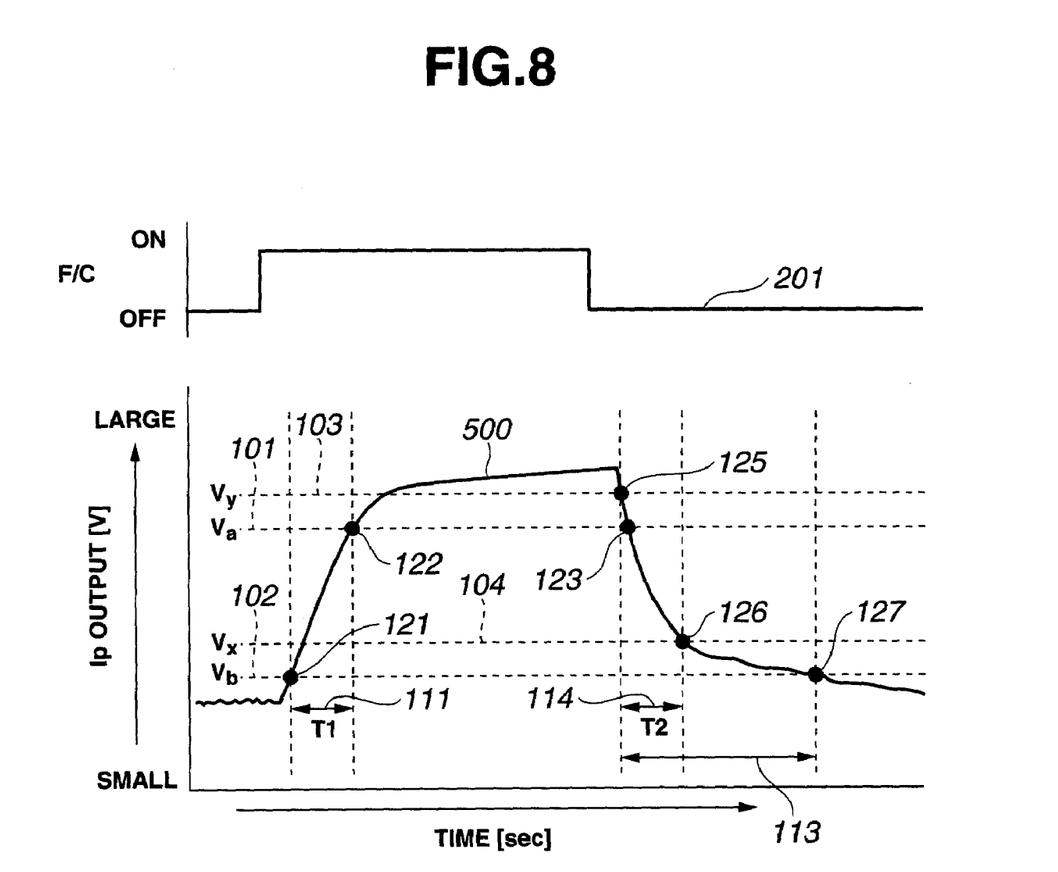
FIG. 8 a graph showing, as an example, a sensor signal showing variation with time of sensor output value outputted from gas sensor unit 3 after a start of interruption of fuel supply (F/C) to an internal combustion engine and after a restart the fuel supply after the F/C.

In a virtual (imaginary) time period of the variation that the sensor output value approaches a stable value corresponding to the atmosphere after the interruption of the fuel supply, the variation speed of the sensor output value becomes gentler during the time period during which the sensor output value is nearer the value corresponding to the atmosphere. On the other hand, in a virtual time period of the variation that the sensor output value returns near the value before the interruption of the fuel supply, the variation speed of the sensor output value becomes gentler during the time period during which the sensor output value is nearer the value before the interruption of the fuel supply. Moreover, the above-mentioned gentle variation speed of the sensor output value may become large for the driving condition and so on of the internal combustion engine. In a range of this extremely gentle variation of the sensor output value, variation of the sensor output value is large even when the gas sensor is in the normal state. FIG. 8 is a graph showing a sensor signal representing a variation of the sensor output value outputted from gas sensor unit 3 after the interruption of the fuel supply to the internal combustion engine and after the restart of the fuel supply after the F/C. FIG. 8 corresponds to FIG. 3, and a sensor signal 500 represents the variation with time that ON/OFF of the F/C is performed at the timing shown by a signal 201. In the virtual time period that the sensor output value returns, after the fuel supply restart, to the value before the start of the fuel supply interruption, sensor signal 500 of FIG. 8 varies gently during the time period near the value before the start of the interruption of the fuel supply. The range of the gentle variation is larger than the sensor signal of FIG. 3. In a case in which the third threshold value and the fourth threshold value is set identical to the values of the first embodiment in FIG. 8, response time period T2 is a time period 113 that the sensor output value varies from a sensor output value 123 to a sensor output value 127. This response time period T2 defined by the third threshold value and the fourth threshold value includes a time period that the sensor output value extremely gently varies, and that the variation of the sensor output value becomes large for the influence of the operating condition and so on of the internal combustion engine.

In this case, the first-fourth threshold values are arbitrarily set so that the ranges for obtaining response time period T1 and response time period T2 do not include the range that the sensor output value extremely gently varies. The range of the gentle variation of the sensor output value that is excluded from the range for obtaining first response time period T1 and second response time period T2 is set in accordance with the use, the characteristics and the accuracy of the abnormal state diagnosis of the gas sensor. In this embodiment, the fourth threshold value of step S565 of FIG. 5 is set to a judgment value Vx (a dotted line 104) which is larger than first threshold value Vb (dotted line 102) of step S520, and which is smaller than second threshold value Va (dotted line 101) of step S530. The third threshold value of step S555 is set to a judgment value Vy (a dotted line 103) which is larger than second threshold value Va. Accordingly, response time period T2 is a time period 114 during which the sensor output value from the sensor output value 125 to the sensor output value 126 are obtained. Accordingly, it is possible to obtain the second time period so as to avoid the time period that the sensor output value extremely gently varies. Accordingly, it is possible to appropriately judge whether or not the gas sensor 2 is in the abnormal state by using the sensor output values after the fuel supply interruption and after the fuel supply restart, without the influence of the operating conditions and so on of the internal combustion engine. In the example of FIG. 8, the fourth threshold value is set larger than the first threshold value, and smaller than the second threshold value, and accordingly response time period T1 and response time period T2 do not include the range that the sensor output value extremely gently varies. In this way, it is preferred that the fourth threshold value is set greater than the first threshold value, and smaller than the second threshold value. For this fourth threshold value, it is possible to increase response time period T1 and response time period T2, and to readily set the threshold value for judging the normal state or the slight deterioration. Therefore, it is possible to accurately diagnoses the abnormal state of gas sensor 2.

In the abnormal state diagnosis method according to the embodiment of the present invention, it is judged whether or not the gas sensor is in the normal state by using the response time period of the accumulation of the first time period and the second time period. The first time period is the time period required for the sensor output value after the interruption of the fuel supply to reach from the first threshold value to the second threshold value. The second time period is the time period required for the sensor output value after the detection of the restart of the fuel supply after the interruption of the fuel supply to reach from the third threshold value to the fourth threshold value. Therefore, it is possible to accurately diagnoses the abnormal state of the gas sensor for the long time period for the diagnosis, relative to the case in which it is judged whether or not the gas sensor is in the abnormal state by using only either the first time period or the second time period. That is, it is possible to enlarge difference between the variations of the sensor output values in the normal state and in the abnormal state (deterioration state) by using the first time period and the second time period. Accordingly, it is possible to readily set the predetermined time period serving as the threshold value for diagnosing whether or not the gas sensor is in the abnormal state, and to accurately perform the abnormal state diagnosis of the gas sensor by using this predetermined time period.

In the case in which the engine speed of the internal combustion engine is not sufficiently large, the concentration of the specified gas component in the exhaust gas discharged from the internal combustion engine is not stable, and accordingly the sensor output value of the gas sensor is not stable. In the abnormal state diagnosis method according to the embodiments of the present invention, in the case in which the engine speed of the internal combustion engine is equal to or lower than the low engine speed judgment threshold value, the abnormal state diagnosis process is not performed. The abnormal state diagnosis of the gas sensor is performed by using the sensor output value in the case in which the concentration of the specified gas component in the exhaust gas is stable. Accordingly, it is possible to improve the accuracy the abnormal state diagnosis.

In the abnormal state diagnosis method according to the embodiments of the present invention, when the sensor output value is not stably outputted, the abnormal state diagnosis process is not performed. Accordingly, the abnormal state diagnosis is not performed by using the sensor output value during the time period during which the sensor output value is not stably outputted, and it is possible to improve the accuracy of the abnormal state diagnosis.

In a virtual (imaginary) time period of the variation that the sensor output value approaches a stable value corresponding to the atmosphere after the interruption of the fuel supply, the variation speed of the sensor output value becomes gentler during the time period during which the sensor output value is nearer the value corresponding to the atmosphere. On the other hand, in a virtual time period of the variation that the sensor output value returns near the value before the interruption of the fuel supply, the variation speed of the sensor output value becomes gentler during the time period during which the sensor output value is nearer the value before the interruption of the fuel supply. Moreover, the above-mentioned gentle variation speed of the sensor output value may become large for the driving condition and so on of the internal combustion engine. In a range of this extremely gentle variation of the sensor output value, variation of the sensor output value is large even when the gas sensor is in the normal state. Accordingly, it is not possible to appropriately judge whether or not the gas sensor is in the abnormal state by the time period during which the sensor output value extremely gently varies. In the abnormal state diagnosis method according to the embodiments of the present invention, the fourth threshold value is greater than the first threshold value, and the third threshold value is greater than the second threshold value. Therefore, it is possible to appropriately judge whether or not the gas sensor is in the abnormal state by using the sensor output values after the fuel supply interruption and after the fuel supply restart, without the influence of the operating conditions and so on of the internal combustion engine.

This application is based on a prior Japanese Patent Application No. 2007-040919 filed on Feb. 21, 2007, and a prior Japanese Patent Application No. 2007-217392 filed on Aug. 23, 2007. The entire contents of the Japanese Patent Applications No. 2007-040919 and No. 2007-217392 are hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. A gas sensor diagnostic method of diagnosing an abnormal state of a gas sensor arranged to output a sensor output value corresponding to a concentration of a specified gas component in an exhaust gas of an internal combustion engine, the gas sensor diagnostic method comprising:
   a fuel supply detecting step of detecting an interruption of a fuel supply to the internal combustion engine, and a restart of the fuel supply after the interruption of the fuel supply;
   a response time period accumulating step of determining a response time period by accumulating a first time period that the sensor output value reaches from a first threshold value to a second threshold value after the detection of the interruption of the fuel supply, and a second time period that the sensor output value reaches from a third threshold value to a fourth threshold value after the detection of the restart of the fuel supply after the interruption of the fuel supply; and
   an abnormal state diagnosing section of determining an abnormal state of the gas sensor when the response time period is greater than a predetermined time period.

2. The gas sensor diagnostic method as claimed in claim 1, wherein the gas sensor diagnostic method further comprises an engine speed obtaining step of obtaining an engine speed of the internal combustion engine, and a diagnosis execution controlling step of controlling so as not to perform the abnormal state diagnosis of the gas sensor by the abnormal state diagnosing step when a first predetermined condition is satisfied; and the first predetermined condition includes a condition that the engine speed obtained by the engine speed obtaining step is equal to or lower than a low engine speed judgment threshold value.

3. The gas sensor diagnostic method as claimed in claim 1, wherein the gas sensor diagnostic method further comprises a sensor output value judging step of judging whether or not the sensor output value is stably outputted, and a diagnosis execution controlling step of controlling so as not to perform the abnormal state diagnosis of the gas sensor by the abnormal state diagnosing step when a second predetermined condition is satisfied; and the second predetermined condition includes a condition that the sensor output value is not stably outputted.

4. The gas sensor diagnostic method as claimed in claim 1, wherein the fourth threshold value is greater than the first threshold value; and the third threshold value is greater than the second threshold value.

5. A gas sensor diagnostic apparatus to diagnose an abnormal state of a gas sensor arranged to output a sensor output value corresponding to a concentration of a specified gas component in an exhaust gas of an internal combustion engine, the gas sensor diagnostic apparatus comprising:
   a fuel supply detecting section configured to detect an interruption of a fuel supply to the internal combustion engine, and a restart of the fuel supply after the interruption of the fuel supply;
   a response time period accumulating section configured to determine a response time period by accumulating a first time period that the sensor output value reaches from a first threshold value to a second threshold value after the detection of the interruption of the fuel supply, and a second time period that the sensor output value reaches from a third threshold value to a fourth threshold value after the detection of the restart of the fuel supply after the interruption of the fuel supply; and
   an abnormal state diagnosing section configured to determine an abnormal state of the gas sensor when the response time period is greater than a predetermined time period.

6. The gas sensor diagnostic apparatus as claimed in claim 5, wherein the gas sensor diagnostic apparatus further comprises an engine speed obtaining section configured to obtain an engine speed of the internal combustion engine, and a diagnosis execution controlling section configured to control so as not to perform the abnormal state diagnosis of the gas sensor by the abnormal state diagnosing section when a first predetermined condition is satisfied; and the first predetermined condition includes a condition that the engine speed obtained by the engine speed obtaining section is equal to or lower than a low engine speed judgment threshold value.

7. The gas sensor diagnostic apparatus as claimed in claim 5, wherein the gas sensor diagnostic apparatus further comprises a sensor output value judging section configured to judge whether or not the sensor output value is stably outputted, and a diagnosis execution controlling section configured to control so as not to perform the abnormal state diagnosis of the gas sensor by the abnormal state diagnosing section when a second predetermined condition is satisfied; and the second predetermined condition includes a condition that the sensor output value is not stably outputted.

8. The gas sensor diagnostic apparatus as claimed in claim 5, wherein the fourth threshold value is greater than the first threshold value; and the third threshold value is greater than the second threshold value.

* * * * *